United States Patent
Baseeth

(10) Patent No.: US 9,155,313 B2
(45) Date of Patent: Oct. 13, 2015

(54) WATER DISPERSIBLE COMPOSITIONS AND METHODS OF USING THE WATER DISPERSIBLE COMPOSITIONS

(71) Applicant: ARCHER DANIELS MIDLAND COMPANY, Decatur, IL (US)

(72) Inventor: Shireen Baseeth, Decatur, IL (US)

(73) Assignee: Archer Daniels Midland Company

( * ) Notice: Subject to any disclaimer, the term of this patent is extended or adjusted under 35 U.S.C. 154(b) by 0 days.

(21) Appl. No.: 14/538,010

(22) Filed: Nov. 11, 2014

(65) Prior Publication Data

US 2015/0065346 A1 Mar. 5, 2015

Related U.S. Application Data

(63) Continuation of application No. 12/017,632, filed on Jan. 22, 2008, now Pat. No. 8,906,431.

(60) Provisional application No. 60/885,970, filed on Jan. 22, 2007.

(51) Int. Cl.
| | | |
|---|---|---|
| *A61K 36/00* | (2006.01) |
| *A61K 31/685* | (2006.01) |
| *A61K 36/31* | (2006.01) |
| *A01N 65/28* | (2009.01) |
| *A61K 36/48* | (2006.01) |
| *A61K 36/55* | (2006.01) |
| *A01N 25/30* | (2006.01) |
| *A01N 65/00* | (2009.01) |
| *A01N 65/08* | (2009.01) |
| *A01N 65/20* | (2009.01) |
| *A01N 65/22* | (2009.01) |

(52) U.S. Cl.
CPC .............. *A01N 65/28* (2013.01); *A01N 25/30* (2013.01); *A01N 65/00* (2013.01); *A01N 65/08* (2013.01); *A01N 65/20* (2013.01); *A01N 65/22* (2013.01); *A61K 36/48* (2013.01); *A61K 36/55* (2013.01)

(58) Field of Classification Search
None
See application file for complete search history.

(56) References Cited

U.S. PATENT DOCUMENTS 4,639,374 A * 1/1987 Matsunobu et al. ............ 426/43
2003/0185946 A1 * 10/2003 Ii et al. .......................... 426/335

FOREIGN PATENT DOCUMENTS

JP 01039941 A * 2/1989
JP 07132222 A * 5/1995

* cited by examiner

*Primary Examiner* — Qiuwen Mi
(74) *Attorney, Agent, or Firm* — Andrew F. Nilles

(57) ABSTRACT

Described herein are compositions comprising a nematicide intermixed with lecithin and a co-surfactant that form stable dispersions in water. Also disclosed are methods of controlling nematodes in soil by application of such compositions.

7 Claims, No Drawings

US 9,155,313 B2

WATER DISPERSIBLE COMPOSITIONS AND METHODS OF USING THE WATER DISPERSIBLE COMPOSITIONS

CROSS-REFERENCE TO RELATED APPLICATIONS

This application is a continuation of U.S. patent application Ser. No. 12/017,632, filed Jan. 22, 2008, which itself claims priority to U.S. Provisional Application No. 60/885,970, filed Jan. 22, 2007, each of the contents of the entirety of which are incorporated by this reference.

TECHNICAL FIELD

This invention is directed towards a process for producing bio-based and bio-degradable pesticides, compositions and uses thereof. The invention also relates to a method for controlling nematodes and pests in grasses and lawns.

BACKGROUND

Nematodes are soil-dwelling, microscopic, un-segmented, round worms that may be parasitic or beneficial to a plant growing in the soil. Depending on the species of the nematode and their numbers in the soil, the nematode may be capable of causing a decline in grasses such as, for instance, turf grass. In established turf grass applications, contact nematicides come in granular or spray formulations and are typically watered-in after application. These nematicides are usually toxic to human and animals and have to be handled with extreme care. Sesame oil has been found as one naturally derived control for the parasitic nematodes which is safe for application. However, sesame oil is not water dispersible. Thus, there is a need for a commercially available spray sesame oil formulation.

Plant parasitic nematodes infect many major food and fiber crops, as well as turf grasses and ornamentals, and cause significant reduction in crop yield and quality. Nematodes have been estimated to cause annual crop losses of about $78 billion worldwide (from the report "Plant & Soil Nematodes: Societal Impact and Focus for the Future", sponsored by USDA-CSRS and The Society of Nematologists). Most plant parasitic nematodes feed on the roots, but a few species attack above-ground plant parts. Damage from nematodes is primarily due to feeding and wounding, which in turn affects water and nutrient absorption, and can lead to secondary infections by bacterial and fungal pathogens. In addition, root-feeding nematodes have been implicated in the transmission of viral diseases. Plant-parasitic nematodes seldom kill plants outright. A loss of yield or quality can occur without specific above-ground symptoms. Sometimes these losses are attributed to other pests, fertility problems, or improper water management. The symptoms of nematode damage may vary among crops and are generally manifested as root galling, lesions, premature wilting, chlorosis and overall reduction in plant vigor.

The most popular means of controlling nematodes include the use of soil fumigants such as methyl bromide, or non-fumigant nematicides such as organophosphates and carbamates. These and most other conventionally used nematicides are toxic to mammals and other non-target organisms, pose a potential threat to the environment and ground water, and may leave chemical residues in food products. Resistant varieties, cultural practices such as rotation, organic amendments, and even biological control have been used with varying degrees of success to control nematodes. In the U.S., there are approximately 13,000 golf courses representing 1.2 million acres and up to 85 million households representing 17 million acres of residential turf. When recreational, commercial, and institutional areas are accounted for, total turf in urban areas is estimated at around 30 million acres. According to the 1998 and 1999 Pesticide Industry Sales and Usage Report, up to 85 million pounds of pesticide active ingredient were applied by consumers for residential pest control while close to 15 million pounds of pesticide active ingredient were professionally applied to golf courses.

Consumers apply pesticides to lawns mainly to control nuisance pests (e.g., ants, fire ants, fleas, stinging insects, and mosquitoes), while commercial lawn care companies focus on pests that damage turf (e.g., grubs, sod webworms, cinch bugs, and European crane fly). Herbicides are applied to control crabgrass and dandelions as well as a variety of other weeds. The use of pesticides on turf poses challenges to human health and the environment. A U.S. Geological Survey analysis of 20 major river basins and aquifer systems reported that insecticides used around homes, gardens, and in commercial and public areas were often found in streams at levels above water quality guidelines. The results of pesticide monitoring of residential runoff indicate that the most widely used and marketed herbicides and insecticides are routinely found in urban runoff in different regions of the country.

According to the United States Environment Protection Agency's Pesticide Incidence Data Reporting System, a total of 31,410 incidents relating to the use of pesticides on lawns were reported over the period between 1995 to 2002. The major categories of incidents were human exposures, domestic animal exposures, and damage to non-target plants. While no severe human incidents were reported for insecticides or herbicides, a large percentage of reports were on minor incidents involving humans. A smaller percentage of reports involved domestic animals or non-target plants. Significant pesticide exposure to humans and the environment can occur because of misuse. Thus, a need exists for a bio-based and bio-degradable nematological composition that is safe for application to plant material and grasses and is not toxic towards mammals.

There are many natural occurring materials which are known effective as herbicides or insecticides. There are many favorable reasons to employ a natural occurring product in the control of undesirable organisms such as soil nematodes. Natural decomposition in the soil and non-injuring to high life forms rank among the most noteworthy. Hence, the use of compositions derived from the sesame plant falls into this category of beneficial, economic and environmental considerations.

Sesame is from the generic *Sesamum*, a member of the Pedaliaceae family. The plant is grown primarily for its seed and oil expressed therefrom. Sesame oil is from sesame seed, of the cultivated *Sesamum indicum*. There are about seventeen wild species reported as occurring in Africa and two in India. *Sesamum indicum* L is an herbaceous plant growing several feet high with a vegetative cycle of only 3 or 4 months. Sesame is one of the highest-yielding, non-perennial oil plants.

Sesame oil is reported as a synergist with certain insecticides—U.S. Pat. No. 2,202,145 (May 28, 1940); U.S. Pat. No. 2,463,324 (Mar. 1, 1949). U.S. Pat. No. 2,463,324 discloses that sesame oil contains a material which is a synergist for certain insecticides, such as pyrethrum.

Sesame oil, meal and extracts of the sesame plant have been found to contain a mixture of unsaponifiable materials such or sesamin, sesamolin and sesamol. U.S. Pat. No. 4,442,092 describes a nematocidal composition containing as an active ingredient(s) therein sesame plant extracts including roots, seeds or stalks, oils and acids extracted therefrom, but primarily sesamin, sesamolin and sesamol. However, the compositions prepared are not stable in water and contain hazardous chemicals such as xylene (see, U.S. Pat. No. 4,442, 092, Column 3 lines 55-60) to produce the emulsifiable concentration formulations. Consequently, a water dispersible nematological or herbicidal composition that is based on bio-degradable and bio-renewable ingredients and that can be sprayed on easily to the land by adding water is needed in the art.

SUMMARY OF THE INVENTION

In one embodiment, a method for controlling nematodes comprises mixing a composition comprising a nematicide, lecithin, and a co-surfactant in water, and placing the composition dispersed in the water in contact with soil.

In another embodiment, a process for producing a product comprises mixing lecithin with a surfactant, thus forming a lecithin-cosurfactant blend, and mixing a nematicide with the lecithin-cosurfactant blend, thus forming a nematicide oil system.

In a further embodiment, a composition comprises a nematicide oil, lecithin and a surfactant.

In still a further embodiment, a composition comprises lecithin, and ethoxylated monoglycerides, fatty acid ethoxylate, or a combination thereof. The composition also includes a nematicide oil.

In another embodiment, a composition comprises a nematicide oil, a non-ionic emulsifier, and a surfactant.

Other embodiments of the present invention will be apparent to those skilled in the art form and from the descriptions, which follow herein.

DETAILED DESCRIPTION

Sesame oil contains varying amounts of linoleic acid, alpha linoleic acid, oleic acid and other fatty acids. The linoleics contained in a composition of the present invention, when applied or incorporated into the soil, may be consumed or absorbed by the parasitic nematode, thus, drying the nematode. This drying will stop feeding and reproductive process of the nematode, thus, reducing or eliminating parasitic nematode populations in the soil having the compositions of the present invention applied thereto. Also, the linoleics and fatty acids of the compositions of the present invention deter or repel most leaf damaging insects due to the unpleasant taste and aroma. The total content of amino acids in sesame oil is about 42 grams per 100 grams. In this amino acid composition, the major composition is methionine and tyrosine. Among the various amino acids present in sesame oil, DL-methionine acts as a nematicide and causes inactivation of the larvae.

In one embodiment, a method for controlling nematodes includes placing a composition comprising a nematicide, lecithin, a co-solvent and a surfactant selected from the group consisting of ethoxylated monoglycerides, fatty acid ethoxylates, polyoxyethylene alkyl ethers, sugar esters, polyglycerol esters, polyoxyethylene alkyl esters, sorbitan alkyl esters, polyoxyethylene sorbitan alkyl esters, glycerol esters, derivatives of any thereof, and any combinations thereof in contact with soil. The composition may also be dispersed in water.

In one embodiment, the nematicide may be an extract of *Sesamum indicum* L and may be used in combination with plant oils including, but not limited to, soybean oil, corn oil, flaxseed oil, cottonseed oil, jatropha oil, canola oil, mustard oil, or combinations of any thereof. Use of a secondary plant oil in certain cases permits lowering of viscosity the composition including the nematicide. Any suitable nematicide agent may be used in place of sesame oil, such as for instance chemically modified plant oils.

In another embodiment, the nematicide may comprise a nematicide oil such as sesame oil, canola oil, mustard oil or any combination thereof.

In still further embodiments, the nematicide oils composition may be used alone or in combination with an essential (herbicidal) oil including, but are not limited to clove oil, thyme oil, rosemary oil, jajoba oil, limonene, peppermint oil, wintergreen oil, vanillin, eucalyptus, lemon grass oil, or combinations of any thereof. These oils have herbicide effects and may have some toxicity to a plant to which they are applied. These oils are typically safe for organic farming. The plant to which a nematicide oil and/or essential may be applied is selected from the group comprising a root vegetable, a tuber vegetable, a bulb vegetable, a cane vegetable, a fruiting vegetable, a leafy vegetable, a curcurbit vegetable, a fruit, a nut, a herb, a row crop, an oil crop, a forage crop, a fiber crop, an ornamental plant, a tree, a flower, a shrub, a bedding plant and a turf grass.

The compositions of the present invention enable the use various nematicide oils, while having a reduced phytotoxic effect on the plants to which they are applied. Thus, in one embodiment, a composition of the present invention comprising a nematicide oil and a surfactant has less phytotoxicity when applied to a plant as compared to a composition including the nematicide oil without the surfactant.

In another embodiment, ethoxylated rapeseed oil derivatives may be used as the nematicide. For instance, neem oil may also be used. Such derivatives are described in Pest Manag Sci 58:1243-1249 (2002); the disclosure of which is incorporated by reference herein in its entirety. In other embodiments, ethoxylated methylated vegetable oils may be used. In yet another embodiment, microbial pathogens or compounds originating from a microbial pathogen may be employed to produce such blends. Such compounds or microbial pathogens may originate from microbes including, but not limited to, the bacteria *Pasteuria penetrans* (formerly known as *Bacillus penetrans*), *Bacillus thuringiensis* (available in insecticidal formulations) and *Burkholderia cepacia*. Other microbial pathogens include without limitation nematicidal fungi such as *Trichoderma harzianum, Hirsutella rhossiliensis, Hirsutella minnesotensis, Verticillium chlamydosporum, Arthrobotrys dactyloides*, and *Paceilomyces lilacinus*. Another fungus, *Myrothecium verrucaria*, found to be highly effective in the control of nematodes, is available in a commercial formulation, DiTera™, from Abbott Laboratories. Circle One, Inc. offers a combination of several mycorrhizal fungal spores in a nematode-control product called Prosper-Nema™. Stein Microbial Products offers the bacterium *Burkholderia cepacia* in a product called Deny™ and Blue Circle™. Rincon-Vitova offers a product called Activate™ whose active ingredient is the bacterium *Bacillus chitinosporus*. Such control methods are described in Nematodes: Alternative Controls (Agriculture Specialist publication #IP287, 2006) published by the National Sustainable Agriculture Information Service (Fayetteville, Ark.); the disclosure of which is incorporated by reference herein in its entirety.

In another embodiment, the lecithin-co-surfactant blends may include a co-solvent such as triglycerides, diglycerides, food grade mineral oils, plant oils, sugar alcohols such as sorbitol, glycerol, ethylene glycol, propylene glycol or any combinations thereof. In yet another embodiment, the lecithin may be crude lecithin, de-oiled lecithin, fluid lecithin or combinations of any thereof. The composition may include about 10 to 50 percent by weight of a surfactant containing nonionic compounds such as ethoxylated monoglycerides, ethoxylated diglycerides, ethoxylated alcohols, sorbitan fatty acid esters, sugar esters, poly glycerol esters or any combinations thereof. The surfactant should have a neutral pH value and an HLB (Hydrophilic-Lipophilic Balance) value of between about 10 and 18. HLB value is a number between 1 and 20 assigned to emulsifiers based on the percent weight of hydrophobe to lipophobe in a molecule. If a stable emulsion of two pure liquids cannot be prepared; to achieve stability, a third component such as an emulsifying agent may be used. Less-stable emulsions eventually separate spontaneously into two liquid layers.

In one embodiment, a lecithin-co-surfactant blend is produced. Such a blend is produced by blending lecithin with a surfactant having a HLB in the range of about 10.0 to 18.0, optionally, in the presence of a co-solvent including, but not limited to, short chain fatty alcohols, acids, ester, glycerols, glycols or any combinations thereof. The co-surfactant blend may include ethoxylated monoglycerides or fatty acid ethoxylate, soybean oil, propylene glycol or any combination thereof. Several surfactants may be used for the blend such as, for example, polyoxyethylene alkyl esters, sorbitan alkyl esters, polyoxyethylene sorbitan alkyl esters, glycerol esters, sugar esters, poly-glycerol esters, derivatives of any thereof or combinations of any thereof. In another embodiment, surfactants which have HLB value of 12 to 16 may be used. The surfactant blend may be produced by mixing lecithin, such as for example fluidized lecithin, crude lecithin or de-oiled lecithin to a composition containing the surfactants and co-solvents. The range of such blends may comprise lecithin between about 50 percent by weight to 90 percent by weight with, the remainder of the blend comprising a co-surfactant.

The lecithin-cosurfactant blend may be intermixed with a nematocidal agent. Levels of such blends that may be used are between about 50 percent to 90 percent by weight of the nematological agent added to the lecithin-co-surfactant blend.

The lecithin-cosurfactant blend or the nematological agent blend with the lecithin-co-surfactant may be achieved by a variety of techniques including, but not limited to, blending, mixing, shear mixing, turbulizing, stirring, homogenizing or any combinations thereof. Typical mixing times for producing these blends may be at least 30 minutes. In another embodiment, a time period of about 30 minutes to 300 minutes at temperatures sufficient to produce uniform mixing may also be used. In one embodiment, temperatures between 25° C. to 60° C. may be used. Such conditions are a result of cause variable effect and may be optimized based on the type and concentrations of co-surfactants used to produce the blends.

The co-surfactant used may also contain propylene glycol, ethylene glycol, glycerol, short chain fatty acids, esters of any thereof, or combinations of any thereof. In one embodiment, the active ingredient is sesame oil, mustard oil, canola oil, combinations of any thereof, or any other effective nematicide agent. The inert ingredients are dissolved and suspended in the oil. Generally, the compositions are typically sold separately and a penetrant (surfactant) is usually combined when used. The final compositions may be diluted in water and sprayed or poured onto the soil. In one embodiment, all ingredients may be in one phase for ease of use and are ready to deliver to the soil just by diluting with water. In various embodiments, concentrations of active ingredient in the aqueous solution may range from 0.1 to 20 percent. It will be apparent by those of ordinary skill in the art that the percentages and approaches to application will vary with the type of crop, type of nematode to treat, and/or other conditions and may be optimized using routine experimentation. The surfactant phase may also include, for example, polyoxyethylene derivatives of sorbitan monoester, such as a polyethylene oxide of sorbitan fatty acid esters (sorbitan monopalmitate, sorbitan monooleate, sorbitan monostearate, etc.). These compounds are available under the tradename of "TWEEN" of Uniqema Company (a Delaware Corporation) such as TWEEN 60 or TWEEN 80. Any other suitable surfactant in the desired HLB range may be used. Such surfactants are available from numerous suppliers such as BASF (Florham Park, N.J.), Lonza (Allendale, N.J.), Stepan (Northfield, Ill.), Kerry (Beloit, Wis.) etc.

In another embodiment, mixed surfactants (surfactant mixtures) in the given HLB range of 10-18 may be used to enhance the solubilization properties of the blend that can improve the efficacy of the nematicide.

Another embodiment of the invention permits the use of hard (e.g., well) water for application to soil. Dispersibility of the composition of the present invention in hard water is important because of the cost associated with treating water to reduce its hardness. Well water which may be very high in mineral (e.g., calcium, magnesium and iron) content may also be used. The compositions may be used at rates such as from 6 pounds per acre to 300 pounds per acre upon dilution in water. In certain cases, the nematicide compositions may be used at rates of one pound per acre or less depending upon the amount necessary to attain effective control by any application technique in which the compositions and nematodes are brought in mutual contact, such as to the foliage of the plant or grass, to the soil itself, to the nematode itself, or other plant pest.

The water soluble compositions of this invention may also be used in conjunction with any biological or chemical agent such as a biocide, fungicide, nematocide, herbicide, pesticide or insecticide that needs to be dispersed in water prior to application. For instance, substances used in crop protection which need to be dispersed in water prior to application may suitably be developed by the teachings of this invention. A suitable blend of the water soluble composition including lecithin and a co-surfactant may be prepared and blended with the biological or chemical agent that is required for application to produce a stable dispersion in water. In one embodiment, the water soluble composition may also be dispersed in hard water.

In another embodiment, the compositions of the present invention are less phytotoxic to plants to which they are applied as compared to commercially available products. For instance, application of some conventional nematicide products results in damage to the plants to which the conventional nematicide products are applied.

In one embodiment, a water dispersible nematological composition that is based on bio-degradable and bio-renewable ingredients that can be easily sprayed on the land by adding water is disclosed. In another embodiment, a method is described for mixing a composition comprising a nematicide, lecithin, and a co-surfactant in water; and placing the composition in water and applying it to soil for control of nematodes. Also, yet another embodiment of this invention describes a process for producing a product, by mixing lecithin with a surfactant, thus forming a lecithin-co-surfactant blend; and mixing an extract of *Sesamum indicum* L with the lecithin-co-surfactant blend, thus forming a sesame oil system.

In other teachings of this invention is described, a composition comprising sesame seed oil; lecithin; and a compound selected from the group consisting of triglycerides, diglycerides, sugar alcohols, ethoxylated monoglycerides, fatty acid ethoxylates, sorbitan monoester, polyoxyethylene alkyl ethers, polyoxyethylene alkyl esters, sorbitan alkyl esters, polyoxyethylene sorbitan alkyl esters, glycerol esters, short chain fatty alcohols, acids, esters, glycerols, glycols, derivatives of any thereof, and combinations of any thereof.

Another aspect of this embodiment is a composition comprising sesame seed oil; lecithin; and a compound selected from the group consisting of sorbitan monostearate, polyoxyethylene ester of rosin, polyoxyethylene dodecyl mono ether, polyoxyethylene-polyoxypropylene block copolymer, polyoxyethylene monolaurate, polyoxyethylene monohexadecyl ether, polyoxyethylene monooleate, polyoxyethylene mono (cis-9-octadecenyl)ether, polyoxyethylene monostearate, polyoxyethylene monooctadecyl ether, polyoxyethylene dioleate, polyoxyethylene distearate, polyoxyethylene sorbitan monolaurate polyoxyethylene sorbitan monooleate, polyoxyethylene sorbitan monopalmitate, polyoxyethylene sorbitan monostearate, polyoxyethylene sorbitan trioleate, polyoxyethylene sorbitan tristearate, polyglycerol ester of oleic acid, polyoxyethylene sorbitol hexastearate, polyoxyethylene monotetradecyl ether, polyoxyethylene sorbitol hexaoleate, fatty acids, tall-oil, hexaester with sorbitol, ethoxylated castor oil, ethoxylated soybean oil, ethoxylated polyoxyethylene sorbitol tetraoleate, fatty acids, tall-oil, mixed esters with glycerol and polyethylene glycol, alcohols, C9-16 and ethoxylated derivatives of any thereof, and combinations of any thereof.

In another embodiment, a composition for dispersing an oil in water consists essentially of lecithin and a compound selected from the group consisting of sorbitan monostearate, polyoxyethylene ester of rosin, polyoxyethylene dodecyl mono ether, polyoxyethylene-polyoxypropylene block copolymer, polyoxyethylene monolaurate, polyoxyethylene monohexadecyl ether, polyoxyethylene monooleate, polyoxyethylene mono(cis-9-octadecenyl)ether, polyoxyethylene monostearate, polyoxyethylene monooctadecyl ether, polyoxyethylene dioleate, polyoxyethylene distearate, polyoxyethylene sorbitan monolaurate polyoxyethylene sorbitan monooleate, polyoxyethylene sorbitan monopalmitate, polyoxyethylene sorbitan monostearate, polyoxyethylene sorbitan trioleate, polyoxyethylene sorbitan tristearate, polyglycerol ester of oleic acid, polyoxyethylene sorbitol hexastearate, polyoxyethylene monotetradecyl ether, polyoxyethylene sorbitol hexaoleate, fatty acids, tall-oil, hexaester with sorbitol, ethoxylated castor oil, ethoxylated soybean oil, ethoxylated polyoxyethylene sorbitol tetraoleate, fatty acids, tall-oil, mixed esters with glycerol and polyethylene glycol, alcohols, C9-16 and ethoxylated derivatives, of any thereof, and combinations of any thereof.

In an addition embodiment, a composition comprising a nematicide oil, a non-ionic emulsifier and a surfactant may be used as a nematicidal agent. In one embodiment, the non-ionic emulsifier may be a phospholipid. In a further embodiment, the non-ionic emulsifier may be fluid lecithin, deoiled lecithin, acetylated lecithin, hydroxylated lecithin, acetylated and hydroxylated lecithin, or combinations of any thereof.

The following non-limiting examples are provided to further describe the invention. Those of ordinary skill in the art will appreciate that several variations these Examples are possible within the spirit of the invention.

EXAMPLES

Example 1

This example describes a method of making a sesame oil blend spray formulation for nematode control. A lecithin-cosurfactant blend was prepared by mixing: lecithin (available from Archer Daniels Midland Company of, Decatur, Ill.) in an amount of 80 percent by weight; ethoxylated monoglycerides (available from BASF, Florham, N.J.) in an amount of 10 percent by weight; propylene glycol in an amount of 2 percent by weight; and soybean oil in an amount of 8 percent by weight. The components of the spray formulation were mixed at 50° C. under constant stirring for between 30 minutes to 60 minutes, thus producing an amber, transparent lecithin-cosurfactant blend.

The lecithin-cosurfactant blend was mixed in an amount of 30 percent by weight with sesame seed oil in an amount of 70 percent by weight, and heated to 50° C. with constant stirring for thirty minutes to obtain a clear, sesame oil system that easily forms a stable milky dispersion in water.

All of the ingredients used in this Example are considered food grade, bio-based and bio-degradable. The resulting emulsion is considered stable when dispersed in hard water for application to plants and grasses.

Example 2

This example describes another method of making sesame oil blend spray formulation for nematode control.

A lecithin-cosurfactant blend was prepared by mixing lecithin (available from Archer Daniels Midland Company Decatur, Ill.) in an amount of 90 percent by weight and fatty acid ethoxylate (available from Stepan, Northfield, Ill.) in an amount of 10 percent by weight. The lecithin and fatty acid ethoxylate are weighed and heated to 50° C. on constant stirring for thirty minutes to obtain an amber, transparent lecithin-cosurfactant blend. The fatty acid ethoxylate used is an agricultural emulsifier and is approved by the EPA as inert ingredient under U.S. EPA §40 CFR 180.910, U.S. EPA §21 CFR 176.210, 175.105. In the second step, weighed amounts of sesame oil and lecithin-cosurfactant blend were mixed and heated to 50° C. under constant stirring for 30 minutes to 60 minutes to obtain a clear sesame oil system that easily forms a stable milky dispersion in water.

Example 3

This example describes another method of making a sesame oil blend spray formulation for nematode control.

A sesame oil blend was prepared by mixing sesame oil in an amount of 60 percent by weight, lecithin (available from Archer Daniels Midland Company Decatur, Ill.) in an amount of 30 percent by weight, with fatty acid ethoxylate (available from Stepan, Northfield, Ill.) in an amount of 10 percent by weight or ethoxylated monoglycerides (available from BASF, Florham, N.J.) in an amount of 10 percent by weight.

The ingredients are weighed and heated to 50° C. under constant stirring for thirty minutes to obtain an amber, transparent sesame oil blend. The fatty acid ethoxylate used herein is an agricultural emulsifier and is approved by the EPA as inert ingredient under U.S. EPA §40 CFR 180.910, U.S. EPA §21 CFR 176.210, 175.105. The clear sesame oil system easily forms a stable milky dispersion in water.

Example 4

This example discloses a method of making an oil spray composition for nematode control. The composition comprises 70% by weight canola oil and 30% by weight of a lecithin-cosurfactant blend.

The composition was produced by preparing the lecithin-cosurfactant blend as follows. Appropriate amounts of lecithin, ethoxylated monoglycerides, propylene glycol and soybean oil necessary to achieve a composition having 80% lecithin by weight; 10% ethoxylated monoglycerides by weight; 2% propylene glycol by weight; and 8% of soybean oil by weight. The ingredients were heated to 50° C. with constant stirring for 30 minutes, thus producing an amber, transparent lecithin-cosurfactant blend.

The oil spray composition was produced by weighing appropriate amounts of canola oil and the lecithin-cosurfactant blend necessary to achieve the oil spray composition having 70% by weight canola oil and 30% by weight of a lecithin-cosurfactant blend. The canola oil and the lecithin-cosurfactant blend were mixed and heated to 50° C. on constant stirring for 30 minutes to obtain a clear, oil spray composition that easily forms a stable, milky dispersion in water.

Example 5

This example discloses a method of making an oil spray composition for nematode control. The composition comprises 70% by weight canola oil and 30% by weight of a lecithin-cosurfactant blend.

The composition was produced by preparing the lecithin-cosurfactant blend as follows. Appropriate amounts of lecithin and fatty acid ethoxylate necessary to achieve a composition having 90% lecithin by weight and 10% fatty acid ethoxylate by weight. The ingredients were heated to 50° C. with constant stirring for 30 minutes, thus producing an amber, transparent lecithin-cosurfactant blend. The fatty acid ethoxylate is an agricultural emulsifier and approved by the United States Environmental Protection Agency as an inert ingredient under 40 CFR 180.910, 21 CFR 176.210 and 21 CFR 175.105.

The oil spray composition was produced by weighing appropriate amounts of canola oil and the lecithin-cosurfactant blend necessary to achieve the oil spray composition having 70% by weight canola oil and 30% by weight of a lecithin-cosurfactant blend. The canola oil and the lecithin-cosurfactant blend were mixed and heated to 50° C. on constant stirring for 30 minutes to obtain a clear, oil spray composition that easily forms a stable, milky dispersion in water.

Example 6

This example discloses a method of making an oil spray composition for nematode control. The composition comprises 70% by weight of a 1:1 blend of canola oil/sesame oil and 30% by weight of a lecithin-cosurfactant blend.

The composition was produced by preparing the lecithin-cosurfactant blend as follows. Appropriate amounts of lecithin, ethyoxylated monoglycerides, propylene glycol and soybean oil necessary to achieve a composition having 80% lecithin by weight; 10% ethoxylated monoglycerides by weight; 2% propylene glycol by weight; and 8% of soybean oil by weight. The ingredients were heated to 50° C. with constant stirring for 30 minutes, thus producing an amber, transparent lecithin-cosurfactant blend.

The oil spray composition was produced by weighing appropriate amounts of the 1:1 blend of canola oil/sesame oil and the lecithin-cosurfactant blend necessary to achieve the oil spray composition having 70% by weight of the canola oil/sesame oil blend and 30% by weight of a lecithin-cosurfactant blend. The canola oil/sesame oil blend and the lecithin-cosurfactant blend were mixed and heated to 50° C. on constant stirring for 30 minutes to obtain a clear, oil spray composition that easily forms a stable, milky dispersion in water.

Example 7

This example discloses a method of making an oil spray composition for nematode control. The composition comprises 70% by weight of a 1:1 blend of canola oil/sesame oil and 30% by weight of a lecithin-cosurfactant blend.

The composition was produced by preparing the lecithin-cosurfactant blend as follows. Appropriate amounts of lecithin and fatty acid ethoxylate necessary to achieve a composition having 90% lecithin by weight and 10% fatty acid ethoxylate by weight. The ingredients were heated to 50° C. with constant stirring for 30 minutes, thus producing an amber, transparent lecithin-cosurfactant blend. The fatty acid ethoxylate is an agricultural emulsifier and approved by the United States Environmental Protection Agency as an inert ingredient under 40 CFR 180.910, 21 CFR 176.210 and 21 CFR 175.105.

The oil spray composition was produced by weighing appropriate amounts of the canola oil/sesame oil blend and the lecithin-cosurfactant blend necessary to achieve the oil spray composition having 70% by weight of the canola oil/sesame oil blend and 30% by weight of a lecithin-cosurfactant blend. The canola oil/sesame oil blend and the lecithin-cosurfactant blend were mixed and heated to 50° C. on constant stirring for 30 minutes to obtain a clear, oil spray composition that easily forms a stable, milky dispersion in water.

Example 8

This example discloses a method of making an oil spray composition for nematode control. The composition comprises 70% by weight mustard oil and 30% by weight of a lecithin-cosurfactant blend.

The composition was produced by preparing the lecithin-cosurfactant blend as follows. Appropriate amounts of lecithin, ethyoxylated monoglycerides, propylene glycol and soybean oil necessary to achieve a composition having 80% lecithin by weight; 10% ethoxylated monoglycerides by weight; 2% propylene glycol by weight; and 8% of soybean oil by weight. The ingredients were heated to 50° C. with constant stirring for 30 minutes, thus producing an amber, transparent lecithin-cosurfactant blend.

The oil spray composition was produced by weighing appropriate amounts of mustard oil and the lecithin-cosurfactant blend necessary to achieve the oil spray composition having 70% by weight mustard oil and 30% by weight of a lecithin-cosurfactant blend. The mustard oil and the lecithin-cosurfactant blend were mixed and heated to 50° C. on constant stirring for 30 minutes to obtain a clear, oil spray composition that easily forms a stable, milky dispersion in water.

Example 9

This example discloses a method of making an oil spray composition for nematode control. The composition comprises 70% by weight mustard oil and 30% by weight of a lecithin-cosurfactant blend.

The composition was produced by preparing the lecithin-cosurfactant blend as follows. Appropriate amounts of lecithin and fatty acid ethoxylate necessary to achieve a composition having 90% lecithin by weight and 10% fatty acid ethoxylate by weight. The ingredients were heated to 50° C. with constant stirring for 30 minutes, thus producing an amber, transparent lecithin-cosurfactant blend. The fatty acid ethoxylate is an agricultural emulsifier and approved by the United States Environmental Protection Agency as an inert ingredient under 40 CFR 180.910, 21 CFR 176.210 and 21 CFR 175.105.

The oil spray composition was produced by weighing appropriate amounts of mustard oil and the lecithin-cosurfactant blend necessary to achieve the oil spray composition having 70% by weight mustard oil and 30% by weight of a lecithin-cosurfactant blend. The mustard oil and the lecithin-cosurfactant blend were mixed and heated to 50° C. on constant stirring for 30 minutes to obtain a clear, oil spray composition that easily forms a stable, milky dispersion in water.

Example 10

This example describes a method of making a composition including an essential oil or extract having herbicidal activity.

In this example, a weighed amount of a nematicide oil(s) (i.e., sesame oil, canola oil, mustard oil, or any combinations thereof), clove oil, and a lecithin-cosurfactant blend were mixed at room temperature with constant stirring for 30 minutes to obtain a clear, clove oil system that easily formed a stable, milky dispersion in water that was stable over a period of several hours.

The lecithin-cosurfactant blend was prepared by the following two methods.

The lecithin-cosurfactant blend was produced as follows. Appropriate amounts of lecithin, ethyoxylated monoglycerides, propylene glycol and soybean oil necessary to achieve a composition having 80% lecithin by weight; 10% ethoxylated monoglycerides by weight; 2% propylene glycol by weight; and 8% of soybean oil by weight. The ingredients were heated to 50° C. with constant stirring for 30 minutes, thus producing an amber, transparent lecithin-cosurfactant blend.

The lecithin-cosurfactant blend was prepared as follows. Appropriate amounts of lecithin and fatty acid ethoxylate necessary to achieve a composition having 90% lecithin by weight and 10% fatty acid ethoxylate by weight. The ingredients were heated to 50° C. with constant stirring for 30 minutes, thus producing an amber, transparent lecithin-cosurfactant blend. The fatty acid ethoxylate is an agricultural emulsifier and approved by the United States Environmental Protection Agency as an inert ingredient under 40 CFR 180.910, 21 CFR 176.210 and 21 CFR 175.105.

Example 11

The composition prepared by Example 10 may be used as a foliar herbicide that may be used to control actively growing, emerged green vegetation. The composition may be applied to vegetation in an amount of a 5-10% dilution rate to 100 gallons of water to achieve a desired application rate. The composition may be used to control annual and perennial broadleaf and grassy weeds, and affects the portions of the plants that are coated with the composition.

Example 12

The composition produced by any of examples 1-10 is diluted with hard water to form a dispersion containing 0.1 percent to 1.0 percent by weight of the emulsion in water. The dispersion was found to be stable over a period of several hours and may be applied in the amount of 0.1 gallons to 1.0 gallons per acre of land area depending upon the nematode control required. For effective nematode control, the dispersion should be applied at least two times per a 12 week cycle. If nematodes persist, the dispersion may be applied every 10 to 15 days depending on the health of the crops/plants to which the dispersion is being applied.

The present invention has been described with reference to certain exemplary embodiments, compositions and uses thereof. However, it will be recognized by those of ordinary skill in the art that various substitutions, modifications or combinations of any of the exemplary embodiments may be made without departing from the spirit and scope of the invention. Thus, the invention is not limited by the description of the exemplary embodiment, but rather by the appended claims as originally filed.

What is claimed is:

1. A composition comprising:
   an oil; and
   a lecithin-co-surfactant blend comprising 50-90% lecithin and a co-surfactant, the co-surfactant having a hydrophilic-lipophilic balance of between 12 and 16 and the blend having a hydrophilic-lipophilic balance value of between 10 and 18;
   wherein the co-surfactant is selected from the group consisting of an ethoxylated monoglyceride, a fatty acid ethoxylate, and combinations of any thereof; and
   wherein the oil, the lecithin, and the co-surfactant are present in the composition in such amounts that upon dispersing the composition in water, a stable emulsion is formed.

2. The composition of claim 1, wherein the oil comprises a plant oil selected from the group consisting of tall-oil, ethoxylated castor oil, ethoxylated soybean oil, soybean oil, corn oil, flaxseed oil, cottonseed oil, jatropha oil, canola oil, mustard oil, and combinations of any thereof.

3. The composition of claim 2, wherein the plant oil comprises the soybean oil.

4. The composition of claim 2, wherein the plant oil comprises the ethoxylated soybean oil.

5. The composition of claim 1, wherein the lecithin is selected from the group consisting of fluidized lecithin, deoiled lecithin, crude lecithin, and combinations of any thereof.

6. The composition of claim 1, further comprising a co-solvent.

7. The composition of claim 6, wherein the co-solvent is selected from the group consisting of short chain fatty alcohols; acids; esters; sugar alcohols including sorbitol, glycerol, ethylene glycol, propylene glycol; triglycerides; diglycerides; food grade mineral oils; plant oils; and combinations of any thereof.

* * * * *